(12) United States Patent
Epple

(10) Patent No.: US 11,331,465 B2
(45) Date of Patent: May 17, 2022

(54) CATHETER PUMP HAVING A PUMP HEAD FOR INSERTION INTO THE ARTERIAL VASCULATURE

(71) Applicant: CardioBridge GmbH, Hechingen (DE)

(72) Inventor: Klaus Epple, Rangendingen (DE)

(73) Assignee: CardioBridge GmbH, Hechingen (DE)

( * ) Notice: Subject to any disclaimer, the term of this patent is extended or adjusted under 35 U.S.C. 154(b) by 165 days.

(21) Appl. No.: 16/484,812

(22) PCT Filed: Feb. 8, 2018

(86) PCT No.: PCT/EP2018/053122
§ 371 (c)(1),
(2) Date: Aug. 8, 2019

(87) PCT Pub. No.: WO2018/146170
PCT Pub. Date: Aug. 16, 2018

(65) Prior Publication Data
US 2019/0358384 A1 Nov. 28, 2019

(30) Foreign Application Priority Data

Feb. 13, 2017 (DE) ..................... 10 2017 102 823.4

(51) Int. Cl.
*A61M 60/135* (2021.01)
*A61M 60/205* (2021.01)
*A61M 60/818* (2021.01)

(52) U.S. Cl.
CPC ........ *A61M 60/135* (2021.01); *A61M 60/205* (2021.01); *A61M 60/818* (2021.01); *A61M 2210/12* (2013.01)

(58) Field of Classification Search
CPC .............. A61M 60/135; A61M 60/205; A61M 60/818; A61M 2210/12
See application file for complete search history.

(56) References Cited

U.S. PATENT DOCUMENTS 4,261,339 A * 4/1981 Hanson ................. A61M 25/10
600/18
4,276,874 A * 7/1981 Wolvek ............. A61M 25/1038
600/18

(Continued)

FOREIGN PATENT DOCUMENTS

DE 10 2013 008159 A1 11/2013
EP 0 768 900 B1 3/2002

(Continued)

*Primary Examiner* — Gary Jackson
*Assistant Examiner* — Alexander M Eisenberg
(74) *Attorney, Agent, or Firm* — Aslan Law, P.C.

(57) ABSTRACT

A catheter pump having a pump head for insertion into the arterial vasculature. The pump head comprises a conveying element, which can be moved from a folded-up insertion position, in which the pump head can be inserted into the arterial vasculature, into a folded-out operating position, and a cage surrounding the conveying element. The cage comprises a distal and a proximal sleeve as well as filaments extending between the sleeves, a support part coupled to the respective sleeve in the axial direction is provided in the region of the distal and/or the proximal sleeve, the support part comprises a peripheral groove, in which a ring element is held in the axial direction, and the sleeve comprises at least one recess, in which the sleeve is welded to the ring element.

14 Claims, 3 Drawing Sheets

(56) References Cited

U.S. PATENT DOCUMENTS

| | | | |
|---|---|---|---|
| 2008/0132748 A1* | 6/2008 | Shifflette | A61M 60/205 600/16 |
| 2009/0062597 A1* | 3/2009 | Shifflette | F04D 3/00 600/16 |
| 2011/0034874 A1* | 2/2011 | Reitan | A61M 60/122 604/151 |
| 2012/0178986 A1* | 7/2012 | Campbell | A61M 60/896 600/16 |
| 2013/0261375 A1* | 10/2013 | Callaway | A61M 5/168 600/16 |
| 2013/0303969 A1* | 11/2013 | Keenan | A61M 60/824 604/9 |
| 2014/0051908 A1* | 2/2014 | Khanal | A61M 60/871 600/17 |
| 2015/0290372 A1* | 10/2015 | Muller | A61M 60/857 600/424 |
| 2016/0022890 A1 | 1/2016 | Schwammenthal et al. | |

FOREIGN PATENT DOCUMENTS

| | | |
|---|---|---|
| EP | 2 308 422 B1 | 6/2013 |
| RU | 2519757 C2 | 6/2014 |
| RU | 2553938 C2 | 6/2015 |
| RU | 2607302 C2 | 1/2017 |

* cited by examiner

CATHETER PUMP HAVING A PUMP HEAD FOR INSERTION INTO THE ARTERIAL VASCULATURE

CROSS-REFERENCE TO RELATED APPLICATIONS

This application claims priority to German Patent Application No. 10 2017 102 823.4 filed on Feb. 13, 2017, and to PCT Application No. PCT/EP2018/053122 filed on Feb. 8, 2018, the entire contents of which are hereby incorporated by reference.

The invention relates to a catheter pump comprising a pump head for insertion into the arterial vasculature such as the aorta or the heart, the pump head having a rotor which has propellers that can be moved from a folded-up insertion position, in which the pump head can be inserted into the arterial vasculature, into a folded-out operating position, in which the rotor can be rotated, and a cage surrounding the propeller, the cage having a distal and a proximal sleeve and filaments which extend between the sleeves. When or before the propellers are folded out, the sleeves are moved toward each other in such a way that the regions of the filaments positioned between the sleeves expand radially outwards, in order to form a space surrounding the folded-out propellers.

Such catheter pumps are known, for example, from EP 0 768 900 B1 or EP 2 308 422 B1. As described in EP 768 900 B1, a rotor which has fold-out propellers can be used as a rotating conveying element, for example. It is also conceivable for differently shaped conveying elements, such as helical spirals, to be used.

Catheter pumps are used as a temporary circulatory support system, in particular in the aorta of patients, especially when the natural heart is unable to provide the body with sufficiently oxygenated blood. The conveying element and the rotor shaft are operated at comparatively high speeds, in the range of from 7,000 to 15,000 rotations per minute. The pump head of the catheter pump can remain in the aorta for a number of days, in particular after surgery.

The present invention addresses the problem of securely arranging the sleeves of the cage on the catheter, such that a reliable expansion is possible.

This problem is solved by means of a catheter pump which has the features of claim 1. The invention therefore provides that, in the region of the distal and/or the proximal sleeve, a support part is provided which is coupled to the sleeve in the axial direction, the support part having a peripheral groove in which a ring element is provided which is held in the axial direction, and the sleeve having at least one recess, via which the sleeve is welded to the ring element.

The proximal support part is preferably motion-coupled to the outer catheter in the axial direction. The distal support part is preferably motion-coupled to the inner catheter in the axial direction. As a result of a relative movement between the inner catheter and the outer catheter, the cage, and ultimately also the conveying element, can thereby be expanded or collapsed.

The welding of the relevant sleeve to the associated ring element has the advantage that the sleeve and the ring element can be made of a different material to the relevant support part. The ring element is arranged in a peripheral groove which is provided in the support part, and held in a form-fitting manner in the axial direction such that it is movable relative to the support part in the axial direction preferably with little or no clearance. In this way it can be ensured that axial forces moving the sleeves toward one another or away from one another are reliably transmitted from the support part to the ring element and thus to the sleeve. The axial coupling of the sleeves to the corresponding support parts is important in order to ensure a functionally reliable folding-out and folding-up of the rotor propellers. The proximal support part is axially moved ultimately by means of axially moving the outer catheter relative to the inner catheter.

Overall, this can ensure a secure connection of the sleeves to the respective support parts by means of the ring elements.

The ring element may in particular be designed as a slotted component, which in particular results in easier assembly and a tolerance compensation.

The cage, together with the sleeves and the ring element, are preferably made of the same material, and in particular of a shape memory alloy. As a result, the components can be welded in a comparatively simple manner. The support part is preferably made of a different material to the cage, and is preferably made of a stainless steel alloy.

The at least one recess provided in the sleeve is, in particular, a round hole or a slot. The holes can be drilled, stamped or laser cut, for example. The recesses are of such a size that the sleeve can be welded to the ring element by means of a suitable welding device.

Advantageously, the cage is integrally formed together with the sleeves, and made of a shape memory alloy. A shape memory alloy in the form of a nickel-titanium alloy has been found to be particularly advantageous. Due to the good deformability and the good corrosion resistance, the alloy is particularly suitable for the cage. The ring element or elements can, as already mentioned, be made of the same alloy.

Advantageously, the relevant sleeve, and in particular the two sleeves, have a plurality of recesses. In particular, the recesses can be arranged equidistantly on a circumferential circular path. It is also conceivable for a plurality of mutually parallel circular paths to have corresponding recesses.

The distal sleeve of the cage, which is provided on the free end of the catheter pump, is preferably arranged on a distal support part by means of an associated ring element, the distal support part forming a pivot bearing receptacle for the distal end of the rotor. On its radially outer side, the support part provides the peripheral groove for the ring element. On its radially inner side, the support part can provide the pivot bearing receptacle for the rotor.

The proximal sleeve is preferably arranged on a proximal support part, the proximal support part having a sliding bearing receptacle, which allows an axial movement between the proximal sleeve and the proximal end of the rotor. Advantageously, a rotor shaft which rotates the rotor during operation and is guided within the catheter engages at the proximal end of the rotor.

The proximal support part can have an outer bushing and a ring which is arranged in the outer bushing and is movably mounted on the proximal end of the rotor. When the two sleeves move toward one another, the ring of the proximal support part slides on the rotor.

Further details and advantageous designs of the invention can be found in the following description, on the basis of which an embodiment of the invention is explained and described in more detail.

Figure 1:
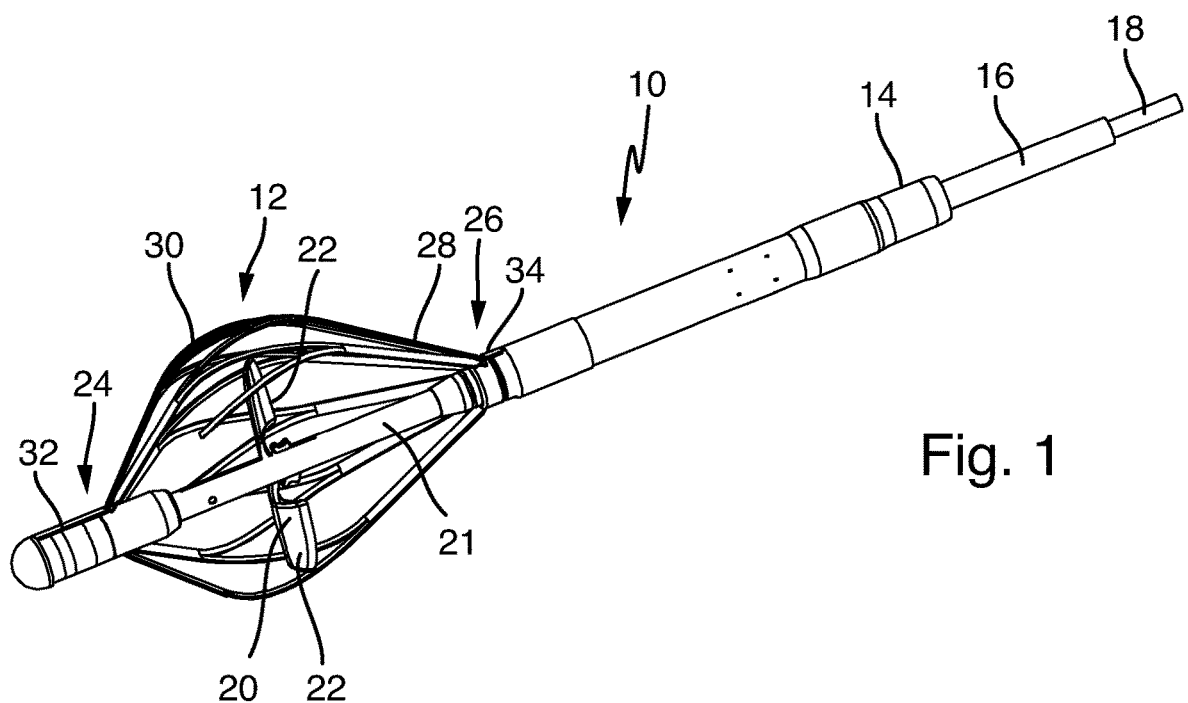
FIG. 1 is a perspective view of a pump head of a catheter pump according to the invention, showing partially-cut sleeves of the cage.

The catheter pump 10 shown in FIG. 1 has a pump head 12 which can be inserted into the aorta or the heart of a patient. The pump 10 comprises an outer catheter 14, an inner catheter 16 and a rotor shaft 18 which is rotatably arranged in the inner catheter 16. A conveying element 20, which is expanded in FIG. 1, in the form of a rotor 21 comprising folded-out propellers 22 can be driven by means of the rotor shaft 18. The propellers 22 are arranged between a distal bearing point 24 and a proximal bearing point 26. The conveying element 20 and the propeller 22 are surrounded by a cage 28, which provides two sleeves 32 and 34 and filaments 30 which extend between the sleeves 32 and 34. In the expanded state, which is shown in FIG. 1, the cage 28 is formed in bulb-like manner, such that the propeller 22 can rotate freely within the cage 28. In order to insert the pump head 12 into the aorta or the heart, the pump head 12 is not expanded, but is in a collapsed or folded-up state. In this collapsed state, the propellers 22 are close to the axis of rotation of the rotor 21 and the filaments 30 of the cage 18 are in a position which extends in parallel with the axis of rotation of the rotor 21.

In order to expand the conveying element 20, the proximal sleeve 34 is moved in the axial direction toward the distal sleeve 32, as a result of which the cage 28 is first moved into the bulb-like position shown in FIG. 1 and the propellers 22 subsequently expand into the folded-out position shown in FIG. 1. The proximal sleeve 34 is moved relative to the distal sleeve 32 by means of an axial movement of the outer catheter 14 relative to the inner catheter 16.

Figure 2:
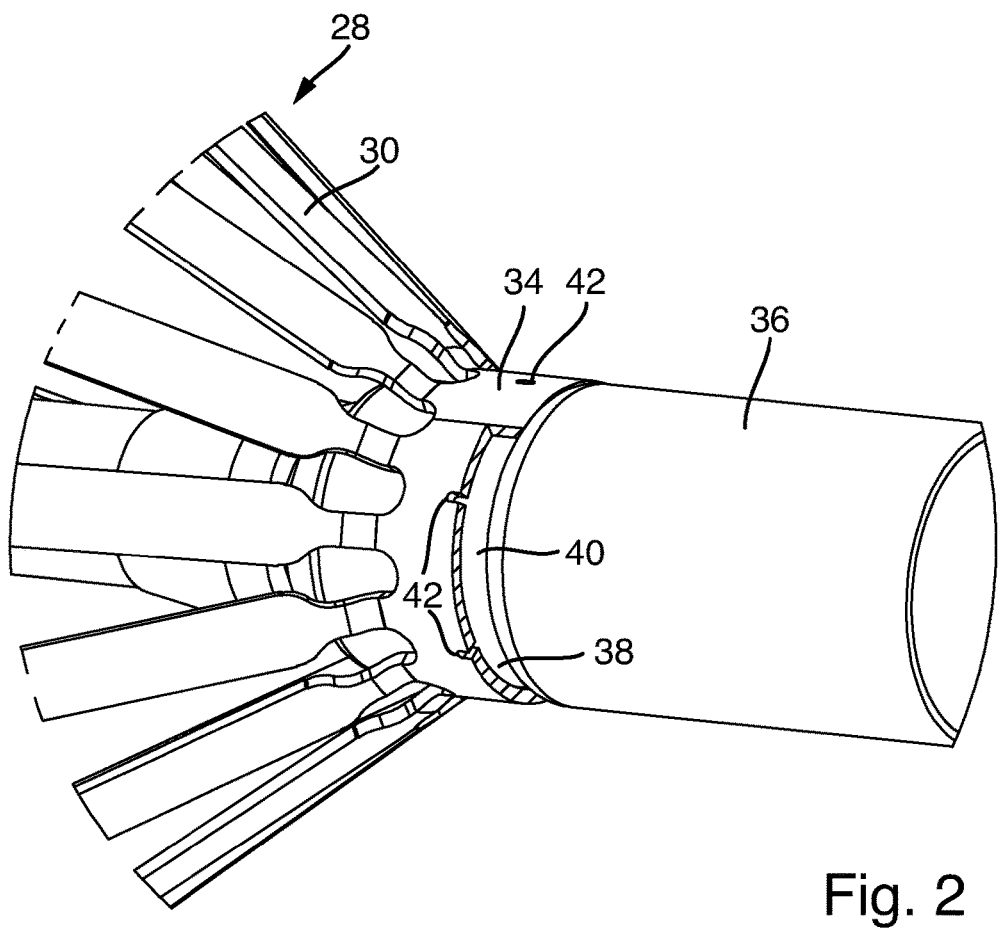
FIG. 2 is an enlarged view of the partially-cut proximal sleeve of the cage.

As is clear from FIG. 2, the distal sleeve 34 of the cage 28 is arranged on a support part 36 by means of a ring element 38. The ring element 38 is located in a peripheral groove 40 which is provided in the support part 36 and is clearly visible in the cross section according to FIG. 4. The ring element 38 is held in the peripheral groove 40 in the axial direction, and in particular is held in the axial direction with zero clearance or at least largely without clearance. In order to connect the sleeve 34 to the ring element 38, the sleeve 34 provides slot-like recesses 42 via which the sleeve 34 is welded to the ring element 38. The cage 28 or ring element 38 is made of the same material as the ring element 38, preferably of a nickel-titanium alloy. Since both components are made of the same material, these components can be welded together in the recesses 42 relatively easily. Since the ring element 38 is arranged in the peripheral groove 40 so as to be held in a form-fitting manner, an axial motion coupling of the sleeve 34 to the support part 36 can be achieved. The support part 36 is preferably made of a stainless steel alloy.

Figure 4:
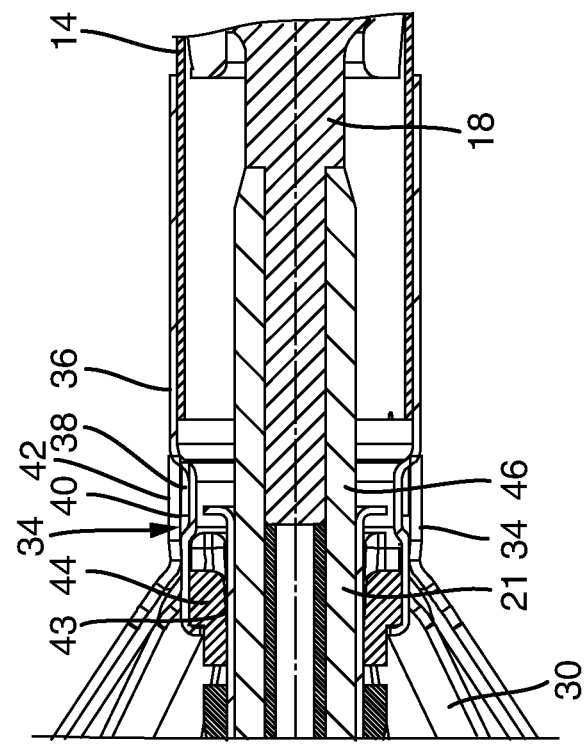
FIG. 4 shows longitudinal sections through the distal and proximal sleeve of the cage.
Figure 4:
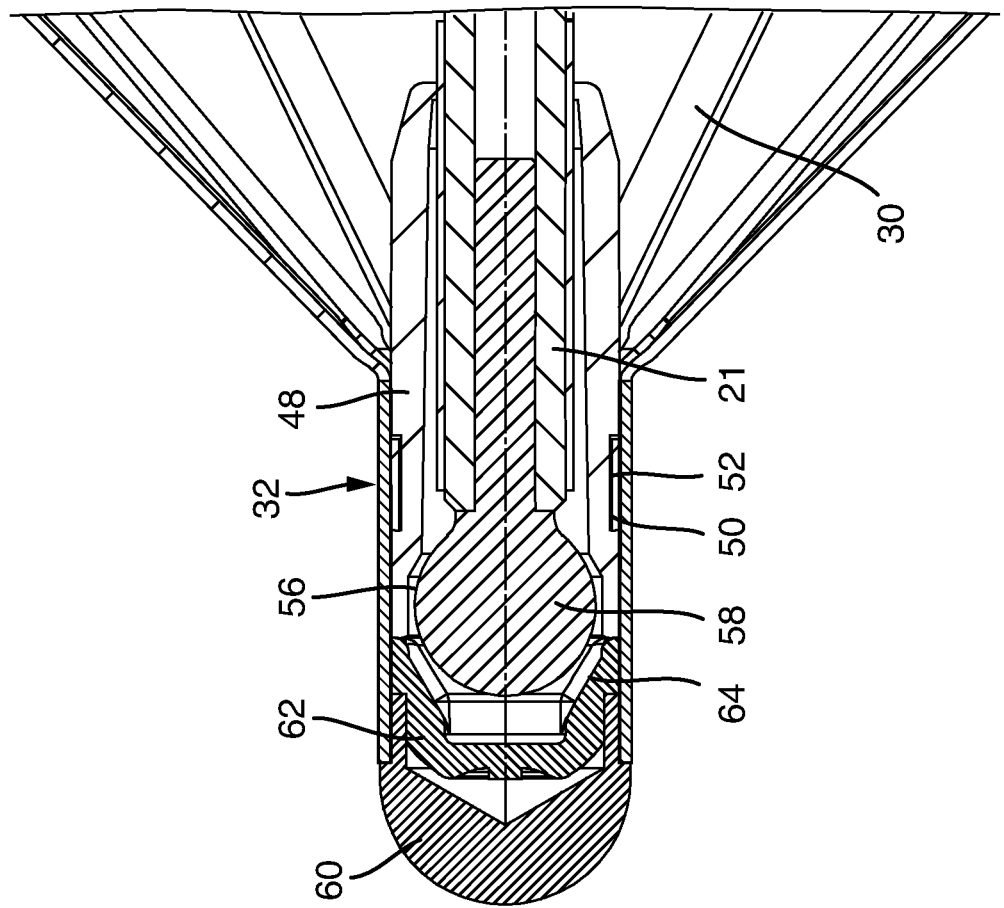

As is clear from FIG. 4, the proximal support part 36 is formed as an outer bushing, with a ring 44 arranged in the outer bushing, which is movably mounted on the proximal end portion of the rotor 21. The ring thus forms a sliding bearing receptacle 43. To collapse or fold-up the cage 28, the proximal sleeve 34 is moved relative to the rotor 21 in the direction facing away from the distal sleeve 32, the ring element 44 then being slidably guided on the proximal region 46 of the rotor 21. The proximal support part 36 is moved on the rotor 21 by means of moving the outer catheter 14 relative to the inner catheter 16, which is motion-coupled to the rotor 21 in the axial direction.

Figure 3:
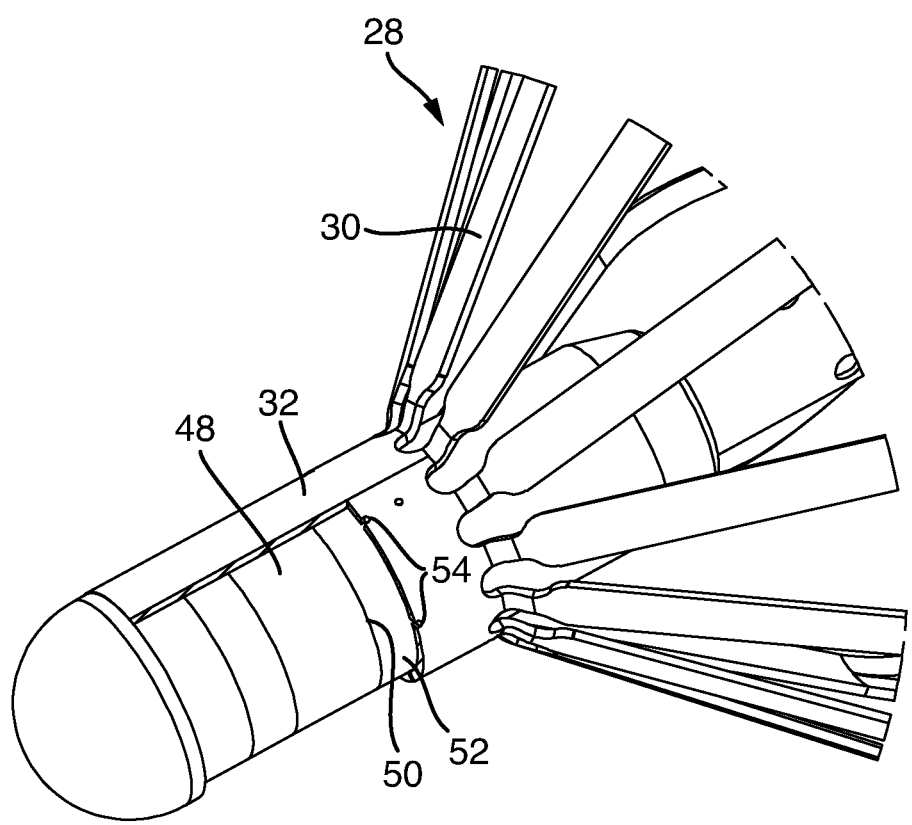
FIG. 3 shows the partially-cut distal sleeve of the cage.

From FIG. 3 it is clear that the distal sleeve 32, corresponding to the proximal sleeve 34, surrounds a distal support part 48, which provides a peripheral groove 50 in which a ring element 52 is mounted or held in the axial direction with zero clearance. The distal sleeve 32, corresponding to the proximal sleeve 34, provides recesses 54 in which welding points are located, by means of which the ring element 52 is in particular spot-welded to the distal sleeve 32.

In FIG. 4, in which the distal support part 48 is shown in longitudinal section, the peripheral groove 50 and the ring element 52 provided in the peripheral groove 50 are clearly visible. In this case, the distal support part 48 has a pivot bearing receptacle 56 for the ball head 58 which is provided at the distal end of the rotor 21. At the distal end, a cap 60 is provided which covers the open end of the sleeve 32. Between the cap 60 and the support part 48, a bearing cap 62 is provided which provides a receiving portion 64 for the ball head 58. The ball head 58 is thus rotatably arranged in a secure manner between the support part 48 and the bearing cap 62.

Although the cage 28 and the sleeves 32 and 34 are made of a different material to the support parts 36 and 48, functionally reliable motion coupling and force transmission in the axial direction can be achieved between the sleeves 32 and 34 and the support parts 36 and 48 by means of the welded connection of the sleeves 32 and 34 to the associated ring elements 38 and 52, and by means of the peripheral grooves 40 and 50 provided in the support parts 36 and 48, in which grooves the ring elements 38 and 52 are arranged in a form-fitting manner.

The invention claimed is:

1. A Catheter pump comprising:
    a pump head for insertion into an arterial vasculature, the pump head having a conveying element that is a rotor with fold-out propellers or that is of a different shape and which is moveable from a folded-up insertion position, in which the pump head is configured to be inserted into the arterial vasculature, into a folded-out operating position; and
    a cage surrounding the conveying element, the cage having a distal sleeve and a proximal sleeve and filaments which extend between the sleeves, wherein
    in the region of the distal sleeve and/or the proximal sleeve, a support part is provided which is coupled to at least one of said sleeves in an axial direction, the support part having a peripheral groove in which a ring element is provided which is held in the groove in a form-fitted manner in the axial direction,
    said at least one of said sleeves and the ring element are made of a different material than that of the support part,
    said at least one of said sleeves having a plurality of recesses that are through holes or slots, via which said at least one of said sleeves is welded to the ring element, and
    a proximal support part is motion-coupled to an outer catheter of the catheter pump in the axial direction,
    a distal support part is motion-coupled to an inner catheter of the catheter pump in the axial direction, and
    the cage and/or the conveying element is capable of expanding or collapsing as a result of a relative movement between the inner catheter and the outer catheter.

2. The Catheter pump according to claim 1, wherein the support part is made of a different material than that of the cage.

3. The Catheter pump according to claim 2, wherein said at least one of said sleeves has the plurality of recesses, via which the ring element is welded to said at least one of the sleeves.

4. The Catheter pump according to claim 3, wherein the distal sleeve is arranged on a distal support part, the distal support part having a pivot bearing receptacle for a distal end of a rotor.

5. The Catheter pump according to claim 4, wherein the proximal sleeve is arranged on a proximal support part, the proximal support part having a sliding bearing receptacle for a proximal portion of the rotor.

6. The Catheter pump according to claim 2, wherein the proximal support part has an outer bushing and a ring arranged in the outer bushing, in which the proximal portion of the rotor is movably mounted.

7. The Catheter pump according to claim 1, wherein the cage, together with the sleeves and the ring element, are made of a shape memory alloy.

8. The Catheter pump according to claim 2, wherein the support part is made of a stainless steel alloy.

9. The Catheter pump according to claim 2, wherein the distal sleeve is arranged on a distal support part, the distal support part having a pivot bearing receptacle for a distal end of a rotor.

10. The Catheter pump according to claim 9, wherein the proximal sleeve is arranged on a proximal support part, the proximal support part having a sliding bearing receptacle for a proximal portion of the rotor.

11. The Catheter pump according to claim 1, wherein said at least one of said sleeves has a plurality of recesses, via which the ring element is welded to said at least one of the sleeves.

12. The Catheter pump according to claim 1, wherein the distal sleeve is arranged on a distal support part, the distal support part having a pivot bearing receptacle for a distal end of a rotor.

13. The Catheter pump according to claim 12, wherein the proximal sleeve is arranged on a proximal support part, the proximal support part having a sliding bearing receptacle for a proximal portion of the rotor.

14. The Catheter pump according to claim 1, wherein said different shape is a helical shape.

* * * * *